United States Patent
Jakkula et al.

(10) Patent No.: US 6,470,734 B2
(45) Date of Patent: *Oct. 29, 2002

(54) METHOD AND ARRANGEMENT FOR MEASURING FLUID

(75) Inventors: Pekka Jakkula, Oulu (FI); Esko Tahkola, Kiviniemi (FI); Timo Manninen, Oulu (FI)

(73) Assignee: Metso Field Systems Oy, Helsinki (FI)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/346,360

(22) Filed: Jul. 1, 1999

(65) Prior Publication Data

US 2002/0066304 A1 Jun. 6, 2002

(30) Foreign Application Priority Data

Jul. 3, 1998 (FI) .................................................. 981545

(51) Int. Cl.$^7$ ............................................... G01N 33/34
(52) U.S. Cl. ....................................... 73/53.03; 324/640
(58) Field of Search .............................. 73/53.01, 53.03; 324/639, 640, 641, 642, 643, 644, 645, 646

(56) References Cited

U.S. PATENT DOCUMENTS

| | | | | |
|---|---|---|---|---|
| 3,681,684 A | * | 8/1972 | Busker et al. ........... | 324/58.5 A |
| 4,423,623 A | | 1/1984 | Ho et al. | |
| 4,546,311 A | * | 10/1985 | Knochel ................ | 324/58.4 A |
| 4,755,743 A | * | 7/1988 | Jakkula ................. | 324/58.5 B |
| 4,820,970 A | * | 4/1989 | Swanson ............... | 324/58.5 A |
| 4,888,547 A | | 12/1989 | McGinn et al. | |
| 5,049,823 A | * | 9/1991 | Castel et al. ............ | 324/640 |
| 5,099,697 A | | 3/1992 | Agar | |
| 5,101,163 A | | 3/1992 | Agar | |
| 5,103,181 A | * | 4/1992 | Gaisford et al. ........ | 324/637 |
| 5,333,493 A | * | 8/1994 | Cutmore ............... | 73/73 |
| 5,455,516 A | * | 10/1995 | Jean et al. .............. | 324/639 |
| 5,502,393 A | * | 3/1996 | Yamaguchi et al. ..... | 324/639 |
| 5,581,191 A | * | 12/1996 | Yamaguchi ............ | 324/637 |
| 5,589,642 A | * | 12/1996 | Agar et al. ............. | 73/861.04 |
| 5,600,073 A | * | 2/1997 | Hill ....................... | 73/861.04 |
| 5,675,259 A | | 10/1997 | Arndt et al. | |
| 5,684,250 A | * | 11/1997 | Marsh et al. ........... | 73/227 |
| 5,701,083 A | * | 12/1997 | Goldberg et al. ....... | 324/642 |
| 5,741,979 A | * | 4/1998 | Arndt et al. ............ | 73/861.04 |
| 5,767,685 A | * | 6/1998 | Walker .................. | 324/640 |
| 5,841,288 A | * | 11/1998 | Meaney et al. ......... | 324/639 |
| 5,859,614 A | * | 1/1999 | Paolella et al. ........ | 343/700 MS |
| 5,864,240 A | * | 1/1999 | Hirai et al. ............. | 324/639 |
| 6,012,324 A | * | 1/2000 | Jakkula et al. ......... | 73/19.03 |
| 6,125,688 A | * | 10/2000 | Matula .................. | 73/19.01 |

FOREIGN PATENT DOCUMENTS

DE 44 26 280 A1 2/1996
DE 44 44 248 A1 6/1996

OTHER PUBLICATIONS

The American Heritage® Dictionary of the English Language, Third Edition copyright© 1992 by Houghton Mifflin Company. Electronic version licensed from INSO Corporation; further reproduction and distribution restricted in accordance with the Copyright Law.*

PCT International Search Report; PCT/FI99/00580, completed Nov. 21, 2000.

* cited by examiner

Primary Examiner—Hezron Williams
Assistant Examiner—C D Garber
(74) Attorney, Agent, or Firm—Alston & Bird LLP

(57) ABSTRACT

The invention relates to a method and an arrangement for measuring a fluid. Electromagnetic radiation is used to measure the consistency, flow and/or gas content of a fluid flowing in a process pipe (102). At least two of the measurements are carried out substantially from the same measurement point in the fluid in a measuring tube (202) by utilizing one integrated measuring equipment (200) comprising transmitters and receivers for electromagnetic radiation in order to carry out the aforementioned at least two measurements.

30 Claims, 3 Drawing Sheets

METHOD AND ARRANGEMENT FOR MEASURING FLUID

FIELD OF THE INVENTION

The invention relates to a method for measuring a fluid, wherein the consistency, flow and/or gas content of a flowing fluid is measured by means of electromagnetic radiation.

The invention also relates to an arrangement for measuring a fluid, comprising units for measuring the consistency, flow and/or gas content in order to measure a fluid that flows in a process pipe by means of electromagnetic radiation.

BACKGROUND OF THE INVENTION

Flow measuring equipments are generally used to measure the flow of a fluid in a pipe. There are various types of prior art measuring equipments, which are typically based on such physical phenomena as the Coriolis force, pressure difference and voltage induced by movement of a conductive material in a magnetic field. Further, ultrasound technology has been used to implement measuring equipments based on correlation and the Doppler effect. Microwave technology has also been used to provide flow measuring equipments based on the Doppler effect. There are also arrangements utilizing the correlation of microwaves by means of a metallic process pipe, disclosed for example in U.S. Pat. No. 4,423,623, U.S. Pat. No. 4,888,547 and WO 94/17373. In the arrangements disclosed in U.S. Pat. Nos. 4,423,623 and 4,888,547, the process pipe is used as a waveguide, and variations in the cut-off frequency of the waveguide serve as correlating signals. The arrangement of WO 94/17373 employs the correlation of signals on the same frequency or at least the same frequency band after the signals have propagated through the flowing material.

The manufacture of paper of good quality requires accurate measurement and adjustment of the water or solids content of the papermaking pulp, in other words the pulp consistency. If the consistency of the pulp is too low or too high, the paper web will not remain homogenous and the quality of the finished paper will not be as good as possible.

At present, the gas content and especially the air content of a fluid or a liquid substance are measured mainly by means of methods and devices based on the ultrasound and the measurement of density. In the ultrasound measurement, the ultrasound is transmitted through the fluid to be measured and the attenuation of the ultrasound is measured. The attenuation of the ultrasound is a function of the gas content of the fluid: the higher the gas content the greater the attenuation of the ultrasound. In the paper industry, the gas content of papermaking pulp with a consistency below 2% is typically measured by means of the ultrasound. The quality of the final product, i.e. paper, depends on the quality of the liquid pulp, which, in turn, is partly dependent on the gas content thereof.

BRIEF DESCRIPTION OF THE INVENTION

The purpose of the invention is to provide a method and an apparatus, implementing the method with which the aforementioned problems can be solved. This is achieved with a method of the type described in the introduction, which is characterized in that at least two of said measurements are carried out substantially from the same measurement point in the fluid by utilizing one integrated measuring equipment comprising units for measuring at least said two properties for the transmission and reception of electromagnetic radiation.

The arrangement according to the invention is characterized in that at least two measuring units, intended for the transmission and reception of electromagnetic radiation, from the units for measuring the consistency, flow and/or gas content are integrated into one measuring equipment, which is attached to the pipe and arranged to perform at least two of said measurements substantially from the same measurement point in the fluid.

The method and the arrangement according to the invention provide several advantages. It is possible to measure with one measuring equipment several properties of a fluid, such as a suspension or slurry, from one measurement point in the process, which reduces the costs of mounting the measuring equipment. Further, one measuring equipment requires less cabling than two or more separate measuring equipments. Particularly air mixed in the papermaking pulp also affects the measurement of production that is based on the consistency and the flow, since with a high air content the process pipe is not full as it is assumed to be in the measurement of the production.

BRIEF DESCRIPTION OF THE FIGURES

In the following, the invention will be described in greater detail in connection with preferred embodiments with reference to the accompanying drawings, in which.

DETAILED DESCRIPTION OF THE INVENTION

The arrangement according to the invention is particularly applicable for use in the paper industry without being limited thereto, however.

Figure 1:
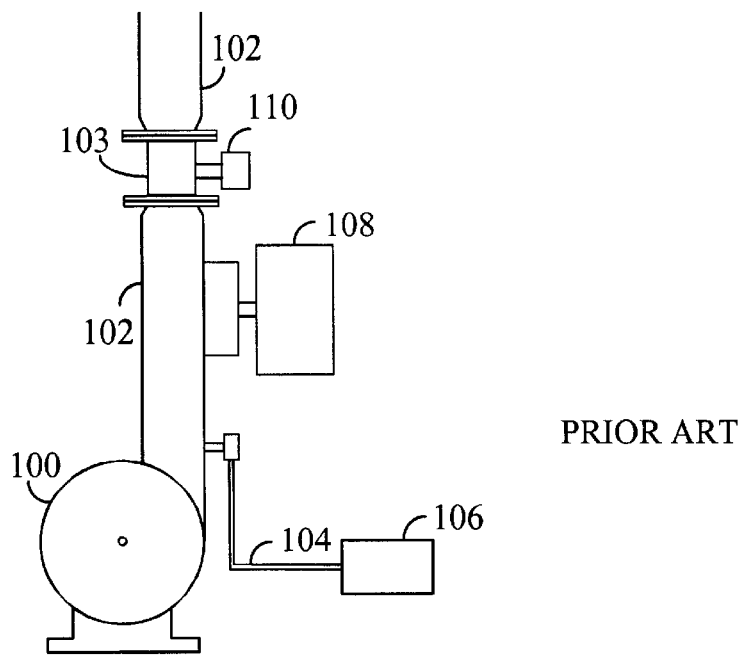
FIG. 1 shows a prior art measuring arrangement.

FIG. 1 shows a prior art arrangement for measuring papermaking pulp. A pump 100 makes the pulp flow in a pipe 102. The air content of the pulp is measured such that a sample is taken from the flowing pulp via a thin tube 104 to an air measuring equipment 106, which operates, for example, by means of the ultrasound. The air content can be measured with the ultrasound if the original consistency of the flowing pulp is less than 2%. The flowing pulp is often thicker, wherefore its consistency must be reduced for the measurement in the sample line. The air content can also be measured by means of density measurement, wherein the density of the flowing pulp is measured from the pulp in the sample line also without reducing the consistency. The consistency of the pulp is measured from a different point in the pipe with another separate measuring equipment, i.e. a consistency measuring equipment 108. Further, the flow of the pulp is measured with a third measuring equipment, a flow measuring equipment 110, which is separate from the other measuring equipments and attached to the pipe 102 via a separate measuring pipe 103.

Figure 2:
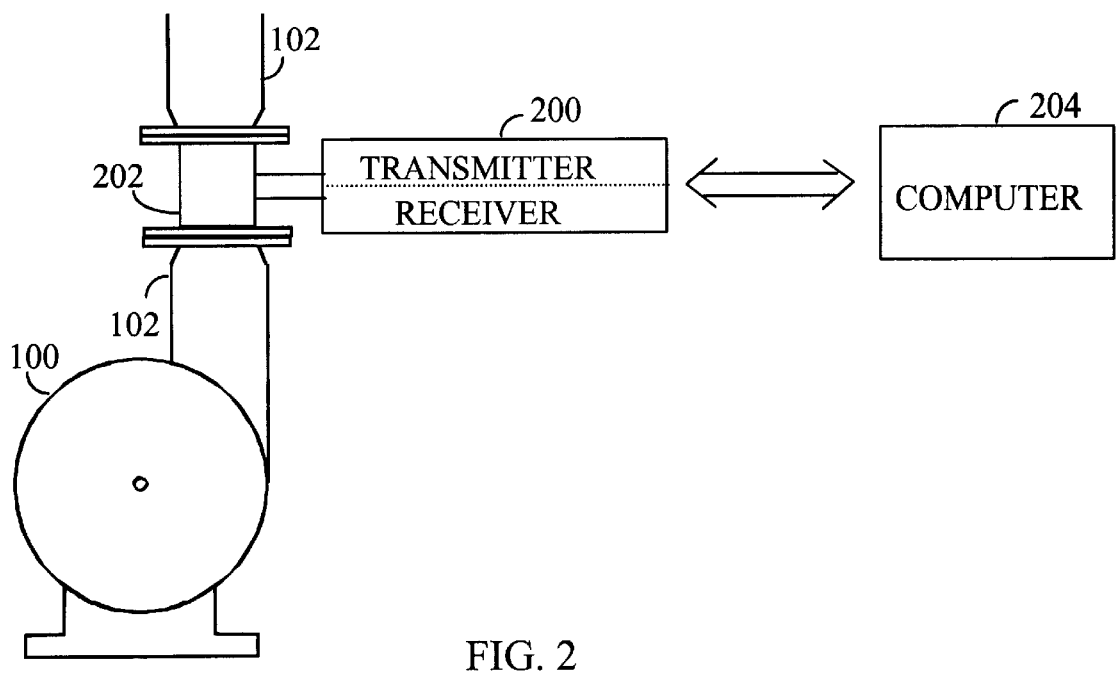
FIG. 2 shows a measuring arrangement according to the invention.

The arrangement according to the invention combines the different measurements of a fluid. In the present application, a fluid refers to any fluid substance which may flow in a pipe, in particular, such as a suspension, slurry, phase mixture or papermaking pulp. The measurements are combined such that at least the transmitters and receivers for the measurement signal are integrated into one unit of the measuring arrangement, which, in turn, is a part of the process pipe. FIG. 2 shows a measuring arrangement according to the invention comprising a pump 100, a pipe 102, a measuring tube 202 and an integrated measuring equipment 200. The integrated measuring equipment may measure the consistency, flow and/or gas content of a flowing fluid. Further, it is possible to integrate into the measuring equipment 200 the measurement of the temperature, pressure and conductivity of the fluid. The measuring equipment 200 can be connected to a computer 204 by means of a known connection, such as RS485, so that the measurement results provided by the measuring equipment 200 can be processed in an automated manner by means of mathematical statistics, for example. The computer 204 is thus able to form a general view of the conditions of flow of the fluid in the process pipe 102 and of the volume of the flow. Further, on the basis of this data the computer 204 can determined the amount of production of the process particularly by means of the flow velocity and the consistency. The amount of production, can be determined more accurately by also utilizing the gas content. The volume flow V can be calculated by multiplying the cross-sectional area A of the measuring tube 202 by the velocity v, in other words V=A*v. The amount of production $T_1$ can be calculated by multiplying the volume flow V by the consistency of the fluid s, in other words $T_1$=V*s. The unit of the production $T_1$ is thus kg/s. The air content is preferably taken into account by multiplying the amount of production $T_1$ by the concentration of the solids and the liquid (1−l), wherein l is the relative gas content, the value of which is in the range [0, . . . , 1]. The actual amount of production $T_0$ is therefore $T_0$=$T_1$*(1−l). The amount of production $T_1$ is often rather close to value $T_0$.

Figure 3A:
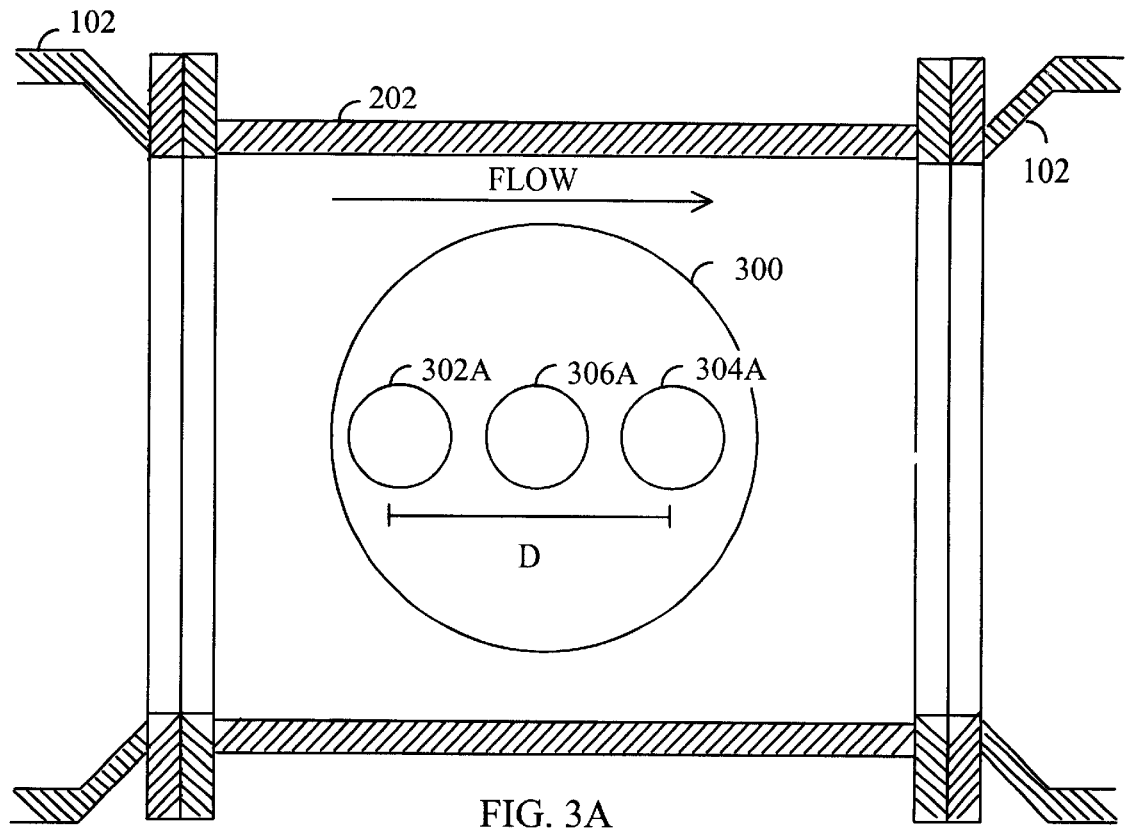
FIG. 3A shows the placing of transmitters and receivers in a process pipe.
Figure 3B:
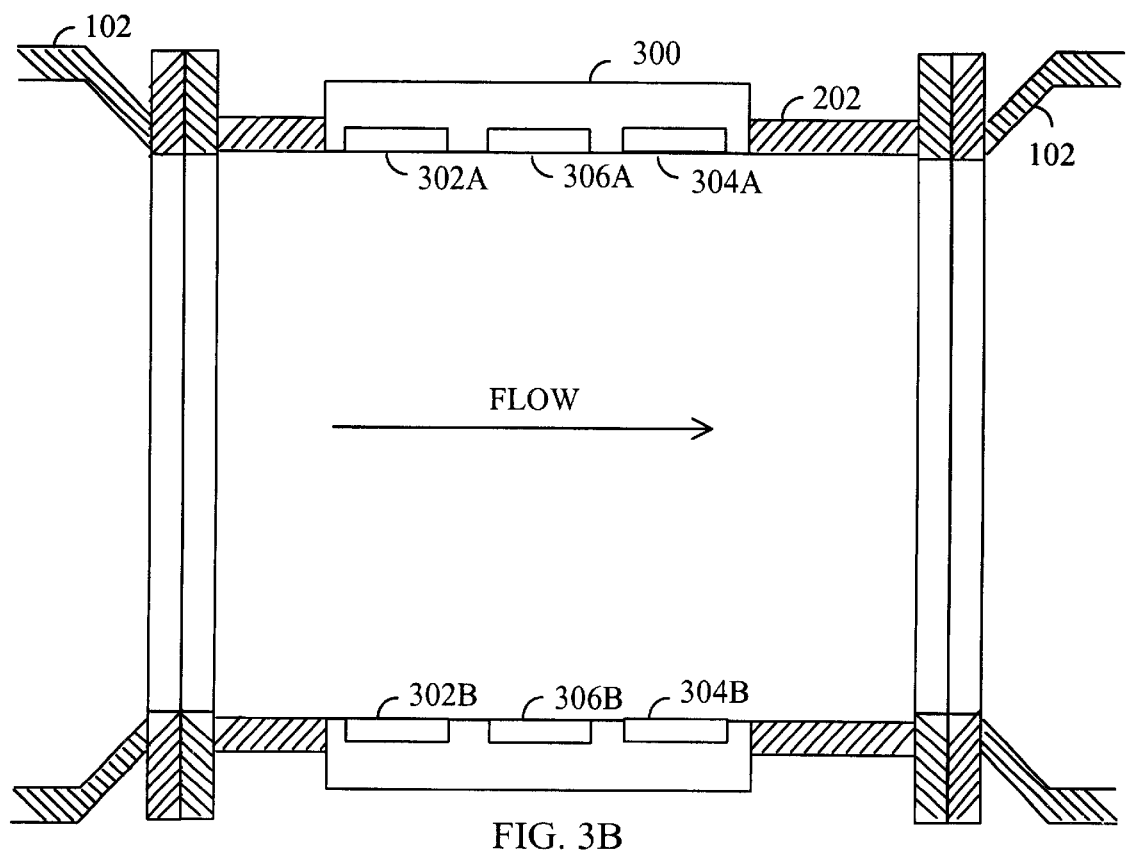
FIG. 3B shows the placing of transmitters and receivers in a process pipe.
Figure 4:
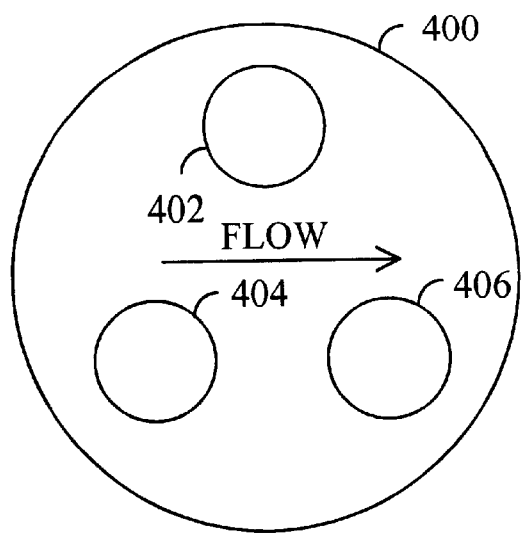
FIG. 4 shows the placing of transmitters and receivers.
Figure 5:
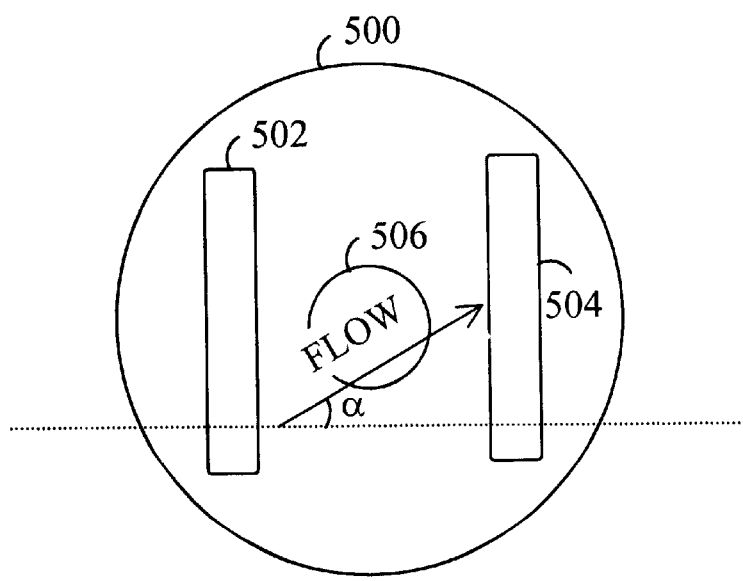
FIG. 5 shows the placing of transmitters and receivers.

In the inventive arrangement, the transmitters and the receivers are integrated together. Especially in the case of microwave technology, the antennas must be integrated into combinations which enable easy measurement of particularly the consistency and the flow velocity of a fluid. The antennas can also be replaced with optical transmitters and receivers. FIGS. 3 to 5 show the, placing and the shapes of the antennas. FIGS. 3A and 3B show the cross-section of the measuring tube 202 to be connected to the point of measurement in:the pipe 102 with the inside of the tube 202 visible. The wall of the measuring tube 202 is provided with a support structure 300, which is a part of the measuring equipment 200 and comprises three antennas 302A–306A or 302B–306B. Antennas 302A and 302B, and 304A and 304B measure the flow of the fluid in the measuring tube 202 preferably by means of correlation. The measurement is carried out, for example in the following manner. Antenna 302A transmits a signal to the fluid, and antenna 302B situated on the opposite side of the tube receives the signal which has. passed through the tube and which is subjected to interference caused by the flowing substance. Antenna 304A, which is placed at a distance D from the previous antenna, also transmits a signal to the fluid, and antenna 304B placed on the opposite side of the tube receives the signal which has passed through the tube and which is subjected to interference caused by the flowing substance. In order to determine the flow velocity, the signals received by antennas 302B and 304B are compared to each other at different moments. The signals correlate best with such a time difference between the moments of measurement that is required by the flowing fluid to travel over the distance D between the antennas. The computer 204 or the measuring equipment 200 itself forms the correlation C(τ) generally according to formula (1), as follows.

$$C(\tau)=\int x(t)\cdot y(t-\tau)dt \quad (1)$$

wherein x(t) is the signal of antenna 302 and y(t−τ) is the signal of antenna 304 which is delayed by τ. The value of the correlation is calculated with several delay values such that τϵ[$t_0$, . . . , $t_n$], wherein $t_0$ is the shortest possible delay and $t_n$ is the longest possible delay. The shortest and the longest possible delay determine the highest and the lowest flow velocity that can be measured over the distance D between antennas 302 and 304. The interval between the measurements τϵ[$t_0$, . . . , $t_n$] is determined specifically in each case. The correlation is calculated in the inventive arrangement either analogically (e.g. in the integrated measuring equipment 200) or digitally (e.g. in the computer 204).

Antennas 306A and 306B measure the consistency of a fluid. Particularly in suspensions the travel time, phase and attenuation of a microwave signal are also dependent on the consistency of the fluid. The consistency is preferably measured by means of the same microwave antennas 306A and 306B as the gas content. The microwave measurement requires frequency modulation according to the FMCW (Frequency Modulated Continuous Wave) technique. In the FMCW technique, the frequency of the oscillator is swept linearly over a broad band, as in a radar. The receiver detects the difference between the travel times of the reference signal and the received signal, which is dependent on the consistency, for example. In all liquid and suspension processes the consistency typically changes more slowly than, for example, the pressure variation caused by the pump 100. Therefore the consistency can be measured as an average over a long period of time on the basis of the travel time, whereas the gas content can be measured at considerably shorter intervals (typically less than 1 s) without frequency modulation, for example in the measurement of the signal phase based on the travel time.

FIG. 4 shows an arrangement which corresponds otherwise to FIG. 3 except that antennas 402–406 are positioned at even intervals on the surface of a support structure 400.

In FIG. 5, antennas 502–506 are placed similarly as in FIG. 3, but the shape of antennas 502 and 504 measuring the velocity is elongated and not round. The advantage of such a shape is that the same point in the fluid probably travels past each antenna. An additional advantage is that even though the flow propagates obliquely at an angle α, the correlation measurement automatically measures the velocity of the flow in the direction of the tube.

The inventive arrangement employs microwave antennas. The antennas are preferably ceramic since the area of such antennas can be made smaller than that of plastic antennas. The diameter of a round antenna may be, for example, Ø24 mm instead of Ø85 mm, as in prior art arrangements.

In the inventive arrangement, the measurements can be carried out also in the form of optical measurements in addition to or instead of microwave measurements. In an optical measurement, antennas 302A–306A and 302B–306B of FIGS. 3A and 3B (correspondingly also the antennas of FIGS. 4 and 5) are replaced with optical transmitters and receivers. In such a case, the transmitter may be any optical power source, such as a lamp, a LED (Light Emitting Diode) or a laser. The receiver, in turn, may be any optical detector, such as a PIN diode or avalance diode. Since the actual optical power transmitter and receiver should not be placed in direct contact with the flowing fluid, antennas 302A–306A and 302B–306B of FIGS. 3A and 3B (correspondingly also the antennas of FIGS. 4 and 5) can be replaced with optical fibres or fibre bundles.

Even though the invention is described above with reference to the examples according to the accompanying drawings, it is clear that the invention is not restricted thereto but it can be modified in various ways within the scope of the inventive idea disclosed in the appended claims.

What is claimed is:

1. A method of measuring the properties of a papermaking pulp located in a pipe, wherein the consistency, flow velocity, and/or gas content of the papermaking pulp is measured by transmitting electromagnetic radiation across a cross-section of the pipe through a cross-section of the papermaking pulp, and measuring the consistency of the papermaking pulp and at least one of the flow velocity and gas content substantially from the same measurement point in the papermaking pulp by utilizing one integrated measuring equipment comprising units for measuring consistency and at least one of said other properties from the transmission and reception of electromagnetic radiation.

2. A method according to claim 1, wherein at least some of the measurements are carried out by means of microwave technology, in which case the measuring units are microwave antennas.

3. A method according to claim 2, wherein the microwave antennas are ceramic.

4. A method according to claim 3, wherein the diameter of the microwave antennas is at most 80 mm.

5. A measuring arrangement according to claim 3, wherein the diameter of the microwave antennas is at most 80 mm.

6. A method according to claim 1, wherein at least some of the measurements are performed optically.

7. A method according to claim 1, wherein the amount of production of the process is formed by measuring at least the consistency and the flow.

8. A method according to claim 7, wherein the amount of production of the process is formed by measuring the consistency, flow and gas content.

9. An apparatus for measuring a papermaking pulp, comprising units for measuring the consistency, flow velocity and/or gas content in order to measure a papermaking pulp that flows in a process pipe by means of transmitting electromagnetic radiation across a cross-section of the pipe through a cross-section of the papermaking pulp, at least two measuring units, intended for the transmission and reception of electromagnetic radiation, said units for measuring consistency, flow velocity and/or gas content being integrated into one measuring equipment, which is attached to the pipe and arranged to measure consistency and at least one of said other properties substantially from the same measurement point in the papermaking pulp.

10. A measuring arrangement according to claim 9, wherein the measuring arrangement is arranged to operate at least partly by means of microwave technology, in which case the measuring units are microwave antennas.

11. A measuring arrangement according to claim 10, wherein the measuring arrangement is arranged to be used for measurement of a fluid flowing in the pipe, and the measuring equipment based on the microwave technology comprises as measuring units microwave antennas, which are integrated into one support structure attached to the pipe.

12. A measuring arrangement according to claim 10, wherein, when the measurement employs microwave technology and the measuring tube is made of metal, the support structure into which the antennas are integrated is arranged to extend onto the inner surface of the measuring tube.

13. A measuring arrangement according to claim 10, wherein, when the measurement employs microwave technology, the antennas are ceramic.

14. A measuring arrangement according to claim 10, wherein, when the measurement employs microwave technology, there are at least two antennas measuring the flow, the antennas are positioned at a predetermined distance from one another, and the antennas are elongated slot antennas.

15. A measuring arrangement according to claim 9, wherein the measuring arrangement is arranged to operate at least partly optically.

16. A measuring arrangement according to claim 9, wherein in order to carry out at least said two measurements substantially from the same measurement point, the measuring equipment is connected to a measuring tube, which is attached to the process pipe.

17. A measuring arrangement according to claim 9, wherein the measuring arrangement is arranged to measure the amount of production of the process by means of measurements of at least the consistency and the flow.

18. A measuring arrangement according to claim 9, wherein the measuring arrangement is arranged to measure the amount of production of the process by means of measurements of the consistency, flow and gas content.

19. A method for measuring at least two individual properties including consistency, flow velocity, and gas content of a papermaking pulp flowing through a pipe by analysis of electromagnetic radiation propagated through the papermaking pulp, wherein said method comprises the steps of:

providing an integrated measuring device including at least two measuring units for transmitting electromagnetic radiation through the papermaking pulp and receiving electromagnetic radiation after it propagates through the papermaking pulp, wherein the at least two measuring units are positioned in close proximity to one another such that the electromagnetic radiation transmitted and received by each measuring unit propagates through the papermaking pulp at substantially the same measurement point on the pipe;

position the integrated measuring device at a selected measurement point on the pipe;

transmitting electromagnetic radiation across a cross-section of the pipe and through a cross-section the papermaking pulp; and determining the consistency of the papermaking pulp and at least one of the flow velocity and gas content of the papermaking pulp using the electromagnetic radiation detected by the at least two measuring units at substantially the same measurement point on the pipe.

20. An integrated measurement device for determining at least two individual properties of a papermaking pulp flowing through a pipe at substantially the same point on the pipe, including the consistency, flow velocity, and gas content of the papermaking pulp, wherein said device comprises:

a measuring tube for connection to a pipe in which the papermaking pulp is flowing; and at least two measuring units positioned in said measuring tube, wherein said measuring units include electromagnetic radiation transtters and receivers configured to transmit electromagnetic radiation across a cross-section of said pipe and through a cross-section of the papermaking pulp and receive electromagnetic radiation after it propagates through the papermaking pulp, wherein said at least two measuring units are positioned in close proximity to one another so as to perform individual measurements on the papermaking pulp at substantially the same measurement point on the pipe, and wherein said measuring units determine the consistency of the papermaking pulp and at least one of flow velocity and gas content of the papermaking pulp based on the individual measurements taken from substantially the same point on the pipe.

21. A method for measuring at least two individual properties of a flowing papermaking pulp by means of electromagnetic radiation, said method comprising:

measuring a consistency of the papermaking pulp; and measuring in addition to consistency at least one of the flow velocity and gas content of the papermaking pulp, wherein said measuring steps are performed at substantially the same measurement point in the liquid using an integrated meter having measuring units that transit electromagnetic ration across a cross-section of the pipe and through a cross-section of the papermaking pulp and receives the electromagnetic radiation after it has passed tough the papermaking pulp, wherein said measuring steps use the electromagnetic radiation received by the measuring units to measure the properties of the papermaking pulp.

22. An integrated measurement device for determining at least two individual properties of a papermaking pulp liquid substance flowing in a pipe including the consistency, flow velocity, and gas content of the papermaking pulp by means of electromagnetic radiation, wherein said device comprises:

measurement units form measuring at least two of the properties of the papermaking pulp that transmit electromagnetic radiation across a cross-section of the pipe and though a cross-section of the papermaking pulp and receives the electromagnetic radiation after it has passed through the papermaking pulp, said measurement units arranged to measure consistency and at leas one of the flow velocity and gas content of the papermaking pulp at substantially the same measurement point.

23. A method for measuring at least two individual properties including consistency, flow velocity, and gas content of a suspension flowing through a pipe by analysis of electromagnetic radiation propagated through the suspension, wherein said method comprises the steps of:

providing an integrated measuring device including at least two measuring units that transmit electromagnetic radiation across a cross-section of the pipe and through a cross-section of the suspension and receive the electromagnetic radiation after it propagates through the suspension, wherein the at least two measuring units are positioned in close proximity to one another such that the electromagnetic radiation tried and received by each measuring unit propagates through the suspension at substantially the same measurement point on the pipe;

positioning the integrated measuring device at a selected measurement point on the pipe; and determining at least two properties of the suspension using the electromagnetic radiation detected by the at least two measuring units at substantially the same measurement point on The pipe.

24. A method according to claim 23, wherein the suspension is papermaking pulp, and wherein said determining step determines at least two properties of the papermaking pulp using the electromagnetic radiation detected by the at least two measuring units at substantially the same measurement point on the pipe.

25. An integrated measurement device for determining at least two individual properties of a suspension flowing through a pipe at substantially the same point on the pipe, including the consistency, flow velocity, and gas content of the suspension, wherein said device comprises:

a measuring tube for connection to a pipe in which the suspension is flowing; and at least two measuring units positioned in said measuring tube, wherein said measuring units include electromagnetic radiation transmitters and receivers configured to transmit electromagnetic radiation across the cross-section of the pipe and through a cross-section of the suspension and receive electromagnetic radiation after it propagates through the suspension, wherein said at least two measuring units are positioned in close proximity to one another so as to perform individual measurements on the suspension at substantially the same measurement point on the pipe, and wherein said measuring units determine the at least two individual properties of the suspension based on the individual measurements taken from substantially the same point on the pipe.

26. A device according to claim 25, wherein one of said measuring units comprises first and second transmitter/receiver sets spaced apart from each other a selected distance which collectively determine the flow velocity of the suspension, and wherein another of said measuring units comprises a third transmitter/receiver set positioned between said first and second transmitter/receiver sets for determining at least one of the consistency and gas content of the suspension.

27. A method for measuring at least two individual properties including consistency, flow velocity, and gas content of a papermaking pulp flowing through a pipe by analysis of electromagnetic radiation propagated through the papermaking pulp, wherein said method comprises the steps of:

providing an integrated measuring device including at least two me units for transmitting electromagnetic radiation across a cross-section of the pipe and through a cross-section of the papermaking pulp and receiving electromagnetic radiation after it propagates through the papermaking pulp, wherein the at least two measuring units are positioned in close proximity to one another such that the electromagnetic radiation transmitted and received by each measuring unit propagates through the papermaking pulp at substantially the same measurement point on the pipe;

positioning the integrated measuring device at a selected measurement point on the pipe; and determining at least two properties of the papermaking pulp using the electromagnetic radiation detected by the at least two measuring units at substantially the same measurement point on the pipe.

28. An integrated measurement device for determining at least two individual properties of a papermaking pulp flowing through a pipe at substantially the same point on the pipe, including the consistency, flow velocity, and gas content of the papermaking pulp, wherein said device comprises;

a measuring tube for connection to a pipe in which the papermaking pulp is flowing; and at least two measuring units positioned in said measuring tube, wherein said measuring units include electromagnetic radiation titters and receivers configured to transmit electromagnetic radiation across a cross-section of the pipe and through a cross-section of the papermaking pulp and receive electromagnetic radiation after it propagates through the papermaking pulp, wherein said at least two measuring units are positioned in close proximity to one another so as to perform individual measurements on the papermaking pulp at substantially the same measurement point on the pipe, and wherein said measuring units determine the at least two individual properties of the papermaking pulp based on the individual measurements taken from substantially the same point on the pipe.

29. A device according to claim 28, wherein one of said measuring units comprises first and second transmitter/receiver sets spaced apart from each other a selected distance which collectively determine the flow velocity of the papermaking pulp, and wherein another of said measuring units comprises a third transmitter/receiver set positioned between said first and second transmitter/receiver sets for determining at least one of the consistency and gas content of the papermaking pulp.

30. An integrated measurement device for determining at least two individual properties of a suspension flowing through a pipe at substantially the same point on the pipe, including the consistency, flow velocity, and gas content of the suspension, wherein said device comprises:

a measuring tube for connection to a pipe in which the suspension is flowing;

an integrated housing connected said tube;

a first measuring unit positioned in said integrated housing, wherein said first measuring unit comprises first and second transmitter/receiver sets spaced apart from each other a selected distance which collectively determine the flow velocity of the suspension; and a second measuring unit comprising a third transmitter/receiver set positioned between said first and second transmitter/receiver sets of said first measuring unit for determining at least one of the consistency and gas content of the suspension.

\* \* \* \* \*

UNITED STATES PATENT AND TRADEMARK OFFICE
CERTIFICATE OF CORRECTION

PATENT NO.      : 6,470,734 B2
DATED           : October 29, 2002
INVENTOR(S)     : Jakkula et al.

It is certified that error appears in the above-identified patent and that said Letters Patent is hereby corrected as shown below:

Column 6,
Line 42, "position" should read -- positioning --;
Line 62, "transtters" should read -- transmitters --.

Column 7,
Line 18, "transit" should read -- transmit --;
Line 19, "ration" should read -- radiation --;
Line 31, "form" should read -- for --;
Line 37, "leas" should read -- least --;
Line 53, "tried" should read -- transmitted --;
Line 62, "The" should read -- the --.

Column 8,
Line 41, "me" should read -- measuring --;
Line 62, after "prises" the semicolon (;) should be a colon (:).

Column 9,
Line 1, "titters" should read -- transmitters --.

Signed and Sealed this

Eighteenth Day of March, 2003

JAMES E. ROGAN
*Director of the United States Patent and Trademark Office*